US006774145B1

(12) United States Patent
Lee et al.

(10) Patent No.: US 6,774,145 B1
(45) Date of Patent: Aug. 10, 2004

(54) MATERIAL SEPARATED FROM ECKLONIA CAVA, METHOD FOR EXTRACTING AND PURIFYING THE SAME, AND USE THEREOF AS ANTIOXIDANTS

(75) Inventors: Bong-Ho Lee, Taejon (KR); Byung-Wook Choi, Taejon (KR); Geon-Seek Ryu, Taejon (KR); Sang-Keun Kim, Kyungki-do (KR); Hyeon-Cheol Shin, Taejon (KR)

(73) Assignee: Ventree Co., Ltd, Seoul (KR)

( * ) Notice: Subject to any disclaimer, the term of this patent is extended or adjusted under 35 U.S.C. 154(b) by 0 days.

(21) Appl. No.: 09/629,341

(22) Filed: Aug. 1, 2000

(30) Foreign Application Priority Data

Apr. 27, 2000 (KR) .......................................... 2000-22593

(51) Int. Cl.[7] ...................... A61K 31/03; A61K 31/075; A61K 35/78; A01N 31/08
(52) U.S. Cl. ........................ 514/732; 514/717; 514/718; 514/723; 514/738; 424/195.17
(58) Field of Search ..................... 424/195.17; 514/185, 514/449, 461, 468, 717, 721, 732, 738, 723, 718

(56) References Cited

U.S. PATENT DOCUMENTS 5,165,933 A  * 11/1992  Oishi

FOREIGN PATENT DOCUMENTS

| JP | 46006373 | * | 2/1971 |
| JP | 56148245 | * | 11/1981 |
| JP | 57033579 | * | 2/1982 |
| JP | 07278003 | * | 10/1995 |
| JP | 2001302655 | * | 10/2001 |

OTHER PUBLICATIONS

Kim et al. J. Korean Fish. Soc. vol. 26, No. 6, pp. 914–916.*
Nakamura et al. Nat. Med. (Tokyo). vol. 51, No. 2, pp. 162–169.*
Iwahori et al. Nat. Med. vol. 53, No. 3, pp. 138–140.*
Lee et al. Korean J. Pharmacognosy. vol. 30, No. 3, pp. 231–237, EMBASE abstract enclosed.*
Taniguchi et al. Nippon Suisan Gakkaishi Bull. of the Jap. Soc. Sci. Fisheries, vol. 58, No. 3, pp 577–581, SCISEARCH Abstract enclosed.*
Park et al., "Separation of Antioxidant Compounds from Edible Marine Algae", *Korean J. Food Sci. Technology*, vol. 23, No. 3, pp. 256–261 (1991).
Nishibori et al., "Antioxidative Activity of Sea Weed Lipids and Their Utilization to Food", vol. 36, No. 11 (1985).
Kaneniwa, et al., "Unusual 5–Olefinic Acids in the Lipids of Algae from Japanese Waters", *Nippon Suisan Gakkaishi*, 53 (5), 861–866 (1987).
"Isolation and Structural Elucidation of an Antioxidative Agent, Naphterpin", The Journal of Antibiotics, vol. XLIII, No. 4, pp. 444–447, (Apr. 1990), Teshima et al.
"Isolation and Structural Elucidation of Pyridoxatin, A Free Radical Scavenger of Microbial Origin", The Journal of Antibiotics, vol. 44, No. 6, pp. 685–687, (Jun. 1991), Shin–Ya et al.
"Isolation and Structural Elucidation of Antioxidative Agents, Antiostatins $A_1$ to $A_4$ and $B_2$ to $B_5$", The Journal of Antibiotics, vol. XLIII, No. 10, pp. 1337–1340, (Oct. 1990).
Miyashita et al., "Tocopherol Content of Japanese Algae and Its Seasonal Variation", *Agric. Biol. Chem.*, 51 (11) 3115–3118, 1987.

* cited by examiner

*Primary Examiner*—Christopher R. Tate
(74) *Attorney, Agent, or Firm*—Abelman, Frayne & Schwab

(57) ABSTRACT

Disclosed are novel materials separated from *Ecklonia cava*, a method for extracting and purifying the same, and the use thereof for antioxidants. The method comprises extracting antioxidative ingredients from powdered *Ecklonia cava* one or more times with an organic solvent; fractionating the antioxidative ingredients one or more times in solvents; and purifying the solvent fractions by chromatography. Superior in scavenging activity and thermal stability, the extract from *Ecklonia cava* can be used as antioxidants and is suitable in commercialization.

8 Claims, No Drawings

MATERIAL SEPARATED FROM ECKLONIA CAVA, METHOD FOR EXTRACTING AND PURIFYING THE SAME, AND USE THEREOF AS ANTIOXIDANTS

BACKGROUND OF THE INVENTION

1. Field of the Invention

This invention relates to materials separated from *Ecklonia cava*, their preparation, and their use as antioxidants. More particularly, the present invention relates to materials extracted from *Ecklonia cava*, which is superior in antioxidative activity and thermal stability, a method for the extraction and purification of such antioxidative materials from *Ecklonia cava*, and use thereof as antioxidants.

2. Description of the Prior Arts

The human body can be maintained alive, utilizing the energy obtained from nutrients through aerobic metabolisms. However, various physical, chemical and biological stresses change oxygen, used as an electron acceptor in aerobic metabolisms, into harmful active oxygen species such as superoxide anion radical ($O_2^-$), hydrogen peroxide, or hydroxy radical to generate fatal physiological disorders or to induce diseases in the human body. The human body possesses an antioxidative mechanism as a self-defense mechanism to scavenge such active oxygen species. However, active oxygen species, if they occur with more potential power than the defense ability of the body, break the factors responsible for the immune system, such as proteins, DNA, enzymes and T cells, to generate disorders. Also, such powerful active oxygen species attack unsaturated fatty acids, which are constituents of cellular membranes, to cause a peroxidation reaction. It is known that lipid peroxides accumulated in the body cause aging and disorders.

There has been widely acknowledged the theory that aging and adult diseases are attributed to active oxygen species. Researches have been directed to the theory since the report on auto-oxidation in the 1940s. Antioxidants, able to inhibit an oxidation reaction, can be used to inhibit acidification of foods, aging of the human body and the like. In particular, synthetic antioxidants, such as butylhydroxytoluene (BHT) and butylhydroxyanisole (BHA), have been extensively used in the food industry. However, these synthetic materials are known to be carcinogenic, so that humans are reluctant to eat such synthetic antioxidant-containing foods. An intensive and extensive interest has been taken in methods for extracting antioxidative materials from natural materials because the extracts do not cause cancers. Of them, a method for extracting beta-carotene from carrots is found to be economically unfavorable because its output is very small. Recently, Shin-Ya et al. have extracted and identify naphtherpin, a kind of antioxidant, from Streptomyces CL 190 (K. Shin-Ya, S, Imai, K. Furihata, Y, Hayakawa, K, Kato, G. D. Vanduyne, J. Clardy and H. Seto, J. Antibiotics 43, 444(1990)), which, however, was not commercialized. Further, Teshima et al. and Mo et al. reported the extraction of antioxidative materials from microorganisms (Y. Techima and K, Shin-Ya, J. Antibiotics 44, 685(1991); C. J. Mo, K. Shin-Ya, K. Furihata, A Shimazu, Y. Hayakawa and H. Seto, J. Antibiotics 43, 1337(1990)), but it was not commercialized, either. In addition, active research efforts have been and continue to be directed to methods for extracting various antioxidative materials from farm products and marine products. Particularly, tocopherol is well-known as an antioxidant, and tea extracts are known to contain various antioxidants. Korean Pat. Publication No. 1997-3067 refers to a method for preparing natural antioxidants by immersing fish skin in hot water to extract gelatin and hydrolyzing the extracted gelatin in a three-step enzyme membrane reactor to obtain enzymatic lysates.

Also, Korean Pat. Application No.99-60007 refers to a method for preparing a natural antioxidant from wild roses, in which the flowers are immersed in an organic solvent to obtain an extract of antioxidative activity from which beta-glucogalin is isolated and purified.

Meanwhile, other attempts to extract physiologically active materials, especially antioxidative materials from seaweeds have been made since late 1980s and have met with success in France and Japan. Tagaki and Miyashida reported that natural compounds extracted from 12 kinds of seaweeds in Japan waters contain tocopherol consisting mainly of an alpha-type along with a minor portion of a beta-type (Miyashita and T. Tagaki, Agric. Biol. Chem. 51, 3115(1987)). Also, Kaneniwa et al. successfully extracted lipid materials of antioxidative activity from seaweeds and identified them as 5-olefinic acids, which are unusual materials in regard to antioxidants (M. Kaneniwa, Y. Itabashi and T Tagaki, Nippon Suisan Gakkashi 53, 861(1987)). Nishibori and Nakami reported that antioxidative lipid materials were extracted from seven kinds of seaweeds with a hexane/ethanol mixture and the lipid materials extracted from lavers and brown seaweeds have an antioxidative activity similar to that of BHA and alpha-tocopherol (S. Nishibori and K. Namiki, kateigaku zaxtusi 36, 17(1985)). But the extracted amount was so small that this method was not commercialized.

It is reported that methanol and chloroform extracts from lavers and brown seaweeds and sea tangles are superior in antioxidative activity to BHA (Jae-Han Park, Gyu-chan Kang, Sang-Bong Paek, Yun-Hyung Lee, Gyu-Soon Lee, Korean Journal of Food Science and Technology 23, 256 (1991)). They used methanol and chloroform, in order, for the extraction of the antioxidative materials from 12 kinds of seaweeds, but failed to commercialize the materials owing to their weak thermal stability.

SUMMARY OF THE INVENTION

In view of these situations, the present inventors have made an extensive research designed to extract and purify useful materials from seaweeds. As a result, the present invention has been completed through the development of novel materials separated from *Ecklonia cava*, which can be used as antioxidants because they have both an excellent antioxidative activity and a thermal stability. In connection, there was also developed a method for extracting and purifying the novel materials of antioxidative activity.

Accordingly, it is an object of the present invention to provide novel materials extracted from *Ecklonia cava*, a kind of seaweed in Korean waters.

It is another object of the invention to provide a method for extracting and purifying such natural materials from *Ecklonia cava*.

It is a further object of the invention to provide use of such natural materials as antioxidants by taking advantage of their superior radical scavenging activity and thermal stability.

Novel materials for achieving said object are represented by the following Formula I.

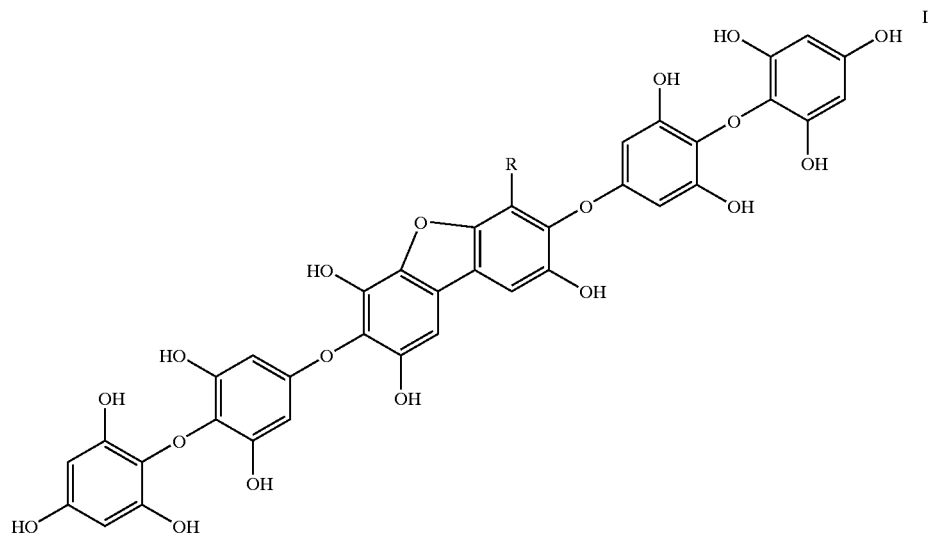

wherein R is hydrogen or a hydroxy group.

To accomplish another object of the present invention, the method for extracting and purifying said materials from *Ecklonia cava*, comprises the following steps; extracting antioxidative ingredients from powdered *Ecklonia cava* one or more times with an organic solvent; fractionating the antioxidative ingredients one or more times in solvents; and purifying the solvent fractions by chromatography.

To accomplish another object of the present invention, novel materials extracted from *Ecklonia cava* are used as antioxidants.

DETAILED DESCRIPTION OF THE INVENTION

Novel materials according to the present invention are represented by the following Formula I, and can be used as antioxidants by virtue of excellent scavenging activity and thermal stability.

The antioxidative materials is extracted and purified as follows.

*Ecklonia cava* is washed with distilled water to eliminate impurities, dried in the absence of direct sunlight, and crushed into powder. At room temperature, this powdered *Ecklonia cava* is immersed in an organic solvent to obtain an extract containing the compound of Formula I. Useful in this extraction is an organic solvent which is preferably selected from the group consisting of methanol, ethanol, ethyl acetate, acetonitrile, acetone, water and a mixture thereof and water/ethanol mixture. Optionally, said extraction procedure may be conducted at least twice in order to increase the yield, wherein a different organic solvent may be used in each repetition step. For eliminating undesired materials and the solvent from the extracts, use can be made of separation and concentration instruments such as a centrifuge and a rotary evaporation concentrator. The extracts obtained

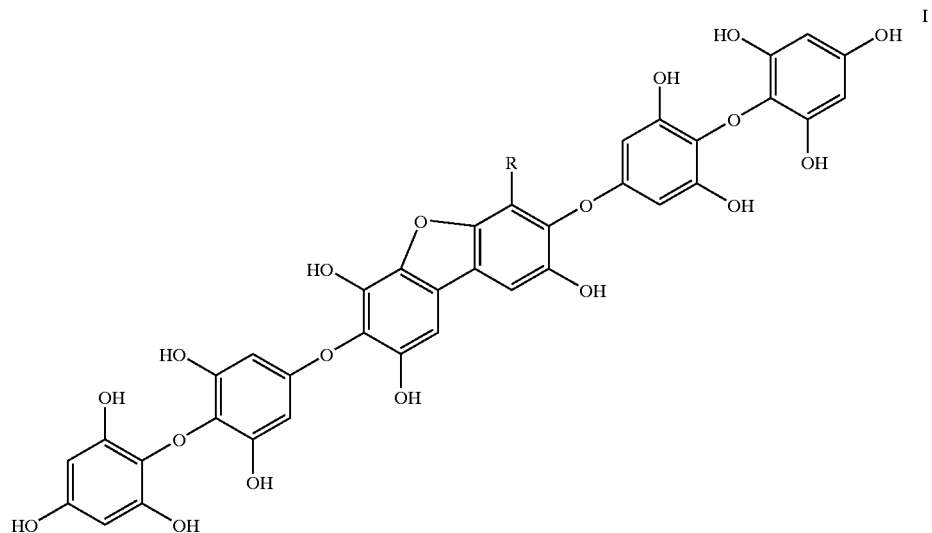

wherein R is hydrogen or a hydroxy group.

through said procedure can be directly used in various fields of applications, so that they are economically favorable because of no additional processes. In the case that the material has to be of high purity, it is preferred that the following additional separation and purification steps are conducted.

The materials obtained from the extraction step are treated in the next fractionation step. Optionally, the method may further comprise the step of dissolving the extracts in ethyl acetate and/or methanol and removing undissolved residues before the fractionation step. By way of examples, and not limitation, the solvent-fractionating step can be conducted in a three-step manner. For a primary fractionation, an aqueous, 10 to 90% methanol solution is used as a polar layer while, as a nonpolar layer, a linear or cyclic hydrocarbon solvent, such as hexane, cyclohexane or pentane and an aromatic solvent, such as benzene or toluene, are used alone or in mixed combinations thereof. In particular, it is preferred to use an aqueous 60 to 90% methanol solution and hexane. As a result of the primary solvent-fractionation, the novel compound dominantly exists in the aqueous methanol solution layer. In a secondary solvent-fractionation, the aqueous solution containing the novel compound is subjected to solvent extraction using an aqueous 10 to 60% methanol solution as a polar layer and one or more ethers including isopropylether as a nonpolar layer. An aqueous 20 to 40% methanol solution and isopropylether are preferred. Likewise, most of the novel compound is found to exist in the aqueous 10 to 60% methanol solution layer. For a tertiary solvent-fractionation, an aqueous 10 to 60% methanol solution is used as a polar layer while, as a nonpolar layer, chloroform and dichloromethane are used alone or in mixed combinations thereof. Preferably, an aqueous 30 to 50% methanol solution and chloroform are used.

For purifying the organic fraction obtained through the above procedure, the aqueous methanol solution layer is re-dissolved in pure distilled water and then passed through membranes to separate active ingredients. Of them, highly active ingredients are collected and purified by, for example, medium pressure liquid chromatography (MPLC) or high performance liquid chromatography (HPLC). In regard to the purification, other chromatographic techniques may be used if necessary.

The antioxidative activity of the novel compound obtained through the extraction and purification process is evaluated by measuring its radical scavenging activity against 1,1-diphenyl-2-picrylhydrazyl (DPPH), which has free radicals attached thereto, according to the Blois method. A thermal stability of the compound of interest can be evaluated by measuring its antioxidative activity at plural temperature points.

A better understanding of the present invention may be obtained in light of the following examples which are set forth to illustrate, but are not to be construed to limit the present invention.

EXAMPLE 1

Extraction Step 410 g of *Ecklonia cava*, which was dried out of direct sunlight and then crushed into powder, was dissolved in 6.5L of methanol in a 1 L round bottom flask and the solution was slowly stirred for 12 hours at room temperature to extract antioxidative materials. Thereafter, the methanol extract was centrifuged at a low temperature to remove undesired impurities, followed by the removal of the methanol with the aid of a rotary evaporation concentrator. The concentrated extract was measured to be 64.1 g.

EXAMPLE 2

Fractionation Step

The extract obtained in Example 1 was dissolved in 4 L of ethyl acetate and concentrated by filtration and then, the undissolved residue was removed. The ethyl acetate solution was subjected to the first solvent-fractionation step of using 1 L of an aqueous 90% methanol solution and 3.5 L of n-hexane. As a result of this fractionation, antioxidative active ingredients were found in the aqueous methanol solution layer. Again, this aqueous solution layer was subjected to the second solvent-fractionation step of using 1 L of an aqueous 30% methanol solution and 1 L of isopropylether. Likewise, the antioxidative active ingredients were in the aqueous 30% methanol solution layer. The third solvent-fractionation step was performed with the aqueous 30% methanol solution layer using 1 L of an aqueous 40% methanol solution and 1 L of chloroform. Thereafter, the aqueous 40% methanol solution layer was dried in vacuo, to give 2.85 g of an organic fraction.

EXAMPLE 3

Purification Step

The organic fraction obtained in Example 2 was loaded in a 25×500 mm glass column filled with ODS (octadecylsilyl) resin with a diameter of 200 $\mu$m and was eluted with a 30% methanol solution to give 850 mg of active ingredients. These active ingredients were subjected to high performance liquid chromatography (acetonitrile:water=20:80, flow rate= 2.0 ml/min, 10×250 mm C-18 column) to give a pure material. Various spectrophotometric analyses were carried out. The results are as follows:

Ultraviolet-visible spectra: UV (MeOH) $\lambda_{max}$ 231 nm ($\epsilon$ 6300), 246, 295 (8800);

Infrared spectra: IR (film) $v_{max}$ 3300 (OH), 2950, 1590 (aromatic) cm$^{-1}$;

Mass spectra: HRFABMS (pos) m/z 745.1039 [(M+H)$^+$, $C_{36}H_{24}O_{18}$, $\Delta$+0.3 mmu]; and $^1$H-NMR: $\delta$ $^1$H (multi, JHz) 6.33 (H, d, 1.6), 6.61 (H, d, 1.6), 6.64 (H, s), 6.64 (H, s), 6.64 (H, s), 6.75 (H, s), 6.80 (H, s), 6.79 (H, s), 6.79 (H, s), 6.22 (H, d, 1.2), 6.66 (H, d, 1.2). From these data, the structure of the material was identified as the following Formula Ia (Dicaval A).

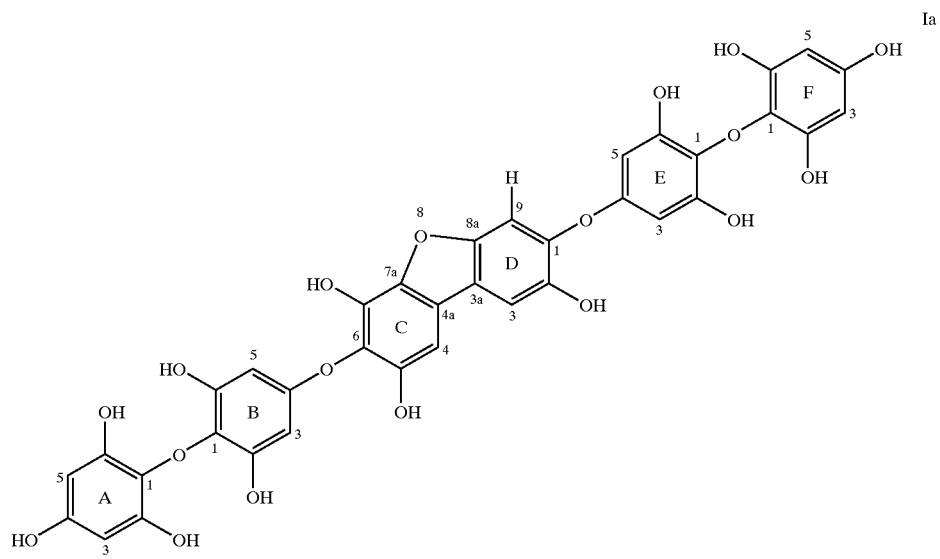

The other was also analyzed in various spectroscopy. The results are as follows:

Ultraviolet-visible light spectra UV (MeOH) $\lambda_{max}$ 232 nm: ($\epsilon$ 6500), 246, 296 (9000);

Infrared light spectra: IR (film) $v_{max}$ 3350 (OH), 2950, 1580 (aromatic) $cm^{-1}$;

Mass spectra HRFABMS (pos) m/z: 761.1024 [(M+H)$^+$, $C_{36}H_{24}O_{19}$, $\Delta$+0.4 mmu];

$^1$H-NMR $\delta$ $^1$ H (multi, JHz): 6.33 (H, d, 1.6), 6.61 (H, d, 1.6), 6.64 (H, s), 6.64 (H, s), 6.64 (H, s), 6.75 (H, s), 6.79 (H, s), 6.79 (H, s), 6.22 (H, d, 1.2), 6.66 (H, d, 1.2). From these data, the structure of the material was identified as the following Formula Ib (Dicaval B).

method. For this, an examination was made of the radical scavenging activity of the two compounds against 1,1-diphenyl-2-picrylhydrazyl (DPPH) to which free radicals were attached. First, 20 mg of DPPH was dissolved in 150 ml of ethanol to prepare a DPPH solution. To 600 $\mu$l of the DPPH solution was added with 250 $\mu$l of dimethylsulfoxide (DMSO), diluted with an appropriate amount of ethanol and shaken for 10 seconds, after which this control was adjusted, in absorbance at 517 nm, from 0.94 to 0.97. To 1 ml of the DPPH solution which was adjusted from 0.94 to 0.97 likewise, each of the samples ($\mu$g to mg) was added and then, reacted for 10 min, followed by measuring the absorbance of

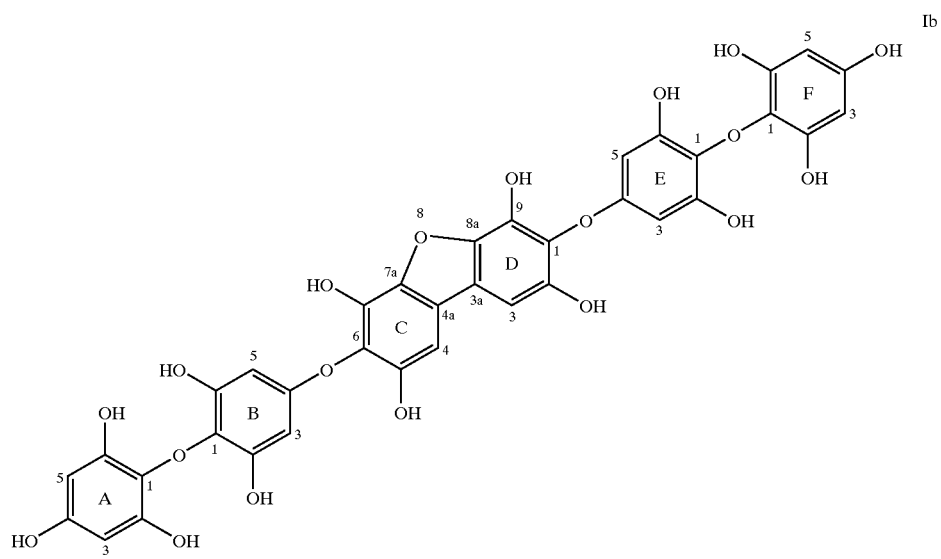

EXAMPLE 4
Measurement of Antioxidative Activity

Dicaval A and Dicaval B obtained in Example 3 were measured for antioxidative activity according to the Blois the solution. The antioxidative activity of each of the samples was determined by the DPPH radical scavenging activity which was represented by a reduced absorbance compared with that of the control.

The antioxidative activity was compared between the conventional antioxidants and the compounds of the invention and the results are given in Table 1, below.

TABLE 1

| Sample amount (μg) | BHT | Dicaval A | Dicaval B | Ascorbic acid |
|---|---|---|---|---|
| 10 | 74% | 100% | 100% | 100% |
| 20 | 87% | 100% | 100% | 100% |
| 100 | 91% | 100% | 100% | 100% |

EXAMPLE 5

Evaluation of Thermal Stability

50 μg of each of Dicaval A and Dicaval B obtained in Example 3 was heated at 40° C., 60° C., 80° C., and 100° C. for 1 hour to measure antioxidative activity. The results are shown in Table 2, below.

TABLE 2

| | Antioxidativity (Absorb. change) | | |
|---|---|---|---|
| Temp. (° C.) | Dicaval A | Dicaval B | Notes |
| 40 | 0.87 | 0.88 | Stable |
| 60 | 0.89 | 0.88 | Stable |
| 80 | 0.88 | 0.87 | Stable |
| 100 | 0.90 | 0.89 | Stable |

From the results of the above tables, it can be said that the antioxidative natural materials of the present invention are superior in antioxidative activity to BHT and excellent, in particular, in thermal stability in the aspect that their antioxidative effects are constantly maintained in a broad range of temperatures.

Over conventional antioxidants, the novel materials of the present invention have advantages of being superior in scavenging activity and thermal stability and showing minimal side effects when administered. Thus, the novel materials can replace the conventional antioxidants.

Whereas particular embodiments of this invention have been described above for purposes of illustration, it will be evident to those skilled in the art that numerous variations of the details of the present invention may be made without departing from the invention as defined in the appended claims.

What is claimed is:

1. A method for preparing an antioxidative compound represented by the following Formula I, which comprises the steps of:

a) extracting *Ecklonia cava* one or more times using at least one solvent selected from the group consisting of methanol, ethanol, ethyl acetate, acetonitrile, acetone, and an aqueous solution thereof;

b) fractionating the extract by using an aqueous 10 to 90% methanol solution as a polar layer, and a linear or cyclic hydrocarbon solvent, an aromatic solvent or a mixture thereof as a nonpolar layer;

c) fractionating the aqueous methanol layer obtained in b) step by using an aqueous 10 to 60% methanol solution as a polar layer and one or more ethers as a nonpolar layer;

d) fractionating the aqueous methanol layer obtained in c) step by using an aqueous 10 to 60% methanol solution as a polar layer and chloroform, dichloromethane, or a mixture thereof as a nonpolar layer; and e) separating and recovering the compound of Formula I from the aqueous methanol layer obtained in step d) by chromatography.

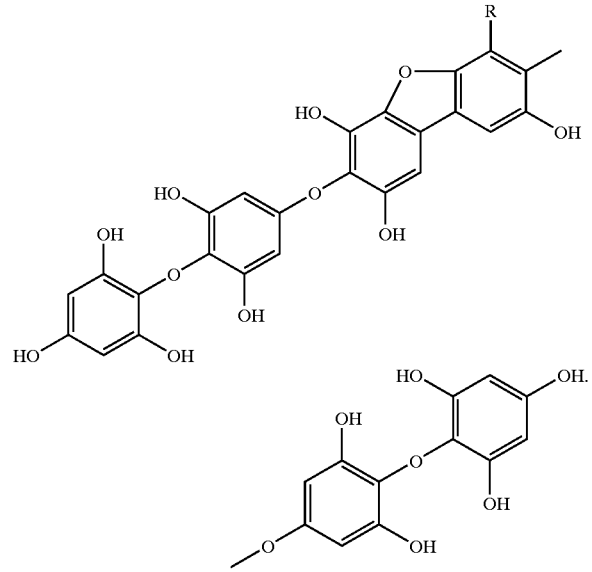

FORMULA I

2. The method as recited in claim 1, wherein step a) is repeated using the same or a different solvent.

3. The method as recited in claim 1, wherein the process further comprises dissolving the extract in ethyl acetate and/or methanol, followed by removing undissolved ingredients therein prior to step c).

4. The method as recited in claim 1, wherein the chromatography is a medium pressure liquid chromatography (MPLC) or a high performance liquid chromatography (HPLC).

5. A method for preparing an antioxidative compound represented by the following Formula I, which comprises the steps of:

a) extracting *Ecklonia cava* one or more times using at least one solvent selected from the group consisting of methanol, ethanol, ethyl acetate, acetonitrile, acetone, and an aqueous solution thereof;

b) fractionating the extract by using an aqueous 10 to 90% methanol solution as a polar layer, and hexane as a nonpolar layer;

c) fractionating the aqueous methanol layer obtained in step b) by using an aqueous 20 to 40% methanol solution as a polar layer and isopropyl ether as a nonpolar layer;

d) fractionating the aqueous methanol layer obtained in step c) by using an aqueous 30 to 50% methanol solution as a polar layer and chloroform as a nonpolar layer; and e) separating and recovering the compound of Formula I from the aqueous methanol layer obtained in step d) by chromatography.

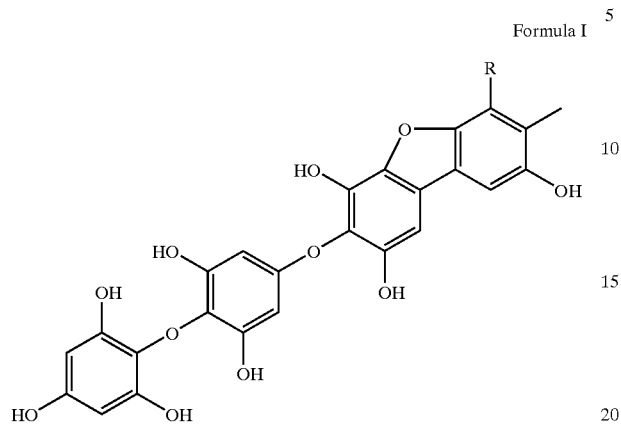

Formula I

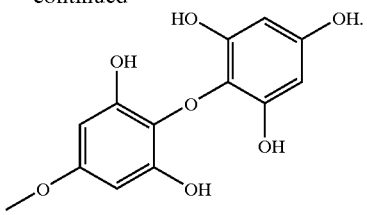

-continued

6. The method as recited in claim 5, wherein step a) is repeated using the same or a different solvent.

7. The method as recited in claim 5, wherein the process further comprises dissolving the extract in ethyl acetate and/or methanol, followed by removing undissolved ingredients therein prior to step c).

8. The method as recited in claim 5, wherein the chromatography is a medium pressure liquid chromatography (MPLC) or a high performance liquid chromatography (HPLC).

* * * * *